United States Patent [19]

Kumamoto

[11] Patent Number: 4,468,460

[45] Date of Patent: Aug. 28, 1984

[54] METHOD OF HUMAN CELL CULTURE

[75] Inventor: Shoichiro Kumamoto, Oita, Japan

[73] Assignee: Chlorella Industry Co., Ltd., Tokyo, Japan

[21] Appl. No.: 380,847

[22] Filed: May 21, 1982

[30] Foreign Application Priority Data

Jun. 15, 1981 [JP] Japan .................................. 56-91733

[51] Int. Cl.$^3$ ........................... C12N 5/00; C12R 1/91
[52] U.S. Cl. .................................... 435/240; 435/948
[58] Field of Search ......................... 435/240, 241, 948

[56] References Cited

U.S. PATENT DOCUMENTS

| | | | |
|---|---|---|---|
| 3,250,606 | 5/1966 | Murray | 47/1.4 |
| 3,520,081 | 7/1970 | Oswald | 47/1.4 |
| 3,820,281 | 6/1974 | Bigler | 47/58 |
| 4,003,156 | 1/1977 | Sibi et al. | 435/240 |
| 4,431,738 | 2/1984 | Maeda et al. | 435/240 |

FOREIGN PATENT DOCUMENTS 0149567 12/1978 Japan ...................................... 71/23

OTHER PUBLICATIONS

Hayflick et al. "The Serial Cultivation of Human Diploid Cell Strains" Experimental Cell Research 25 (1961) p. 585-621.
Jakoby et al., "Cell Culture" Methods in Enzymology vol. LVIII (1979) p. 88-93.
Takada et al., "The Growth Promotive Effect of Extract from Saline-Cultured Chlorella Cells on Halophilic Microorganisms".
Seaweed Symposium Proc. 7 (1972) p. 324-335.
*Practical Tissue Culture Applications*, (1979), edited by Maramorosch and Hirumi, p. 29.
*Botonay*, (Fourth Edition), Wilson and Loomis, p. 400.
*Cell Culture*, (1979), edited by Jakoby, pp. 299-300.
*Industrial Gums*, (1973), edited by Whistler, pp. 30 and 87.

*Primary Examiner*—Thomas Wiseman
*Assistant Examiner*—John Edward Tarcza
*Attorney, Agent, or Firm*—Flynn, Thiel, Boutell & Tanis

[57] ABSTRACT

A method of culture of human cells is disclosed which comprises effecting the cultivation in a culture medium containing an extract of micro algae, such as Chlorella, Scenedesmus or Spirulina, said method permitting the normal successive cultivation of human cells to be maintained efficiently without any morphological and genetic mutations over a greater number of successive of generations than has hitherto been possible even by the incorporation of animal serum in the culture medium, even when the addition amount of such animal serum is reduced substantially or animal serum is completely excluded.

17 Claims, 1 Drawing Figure

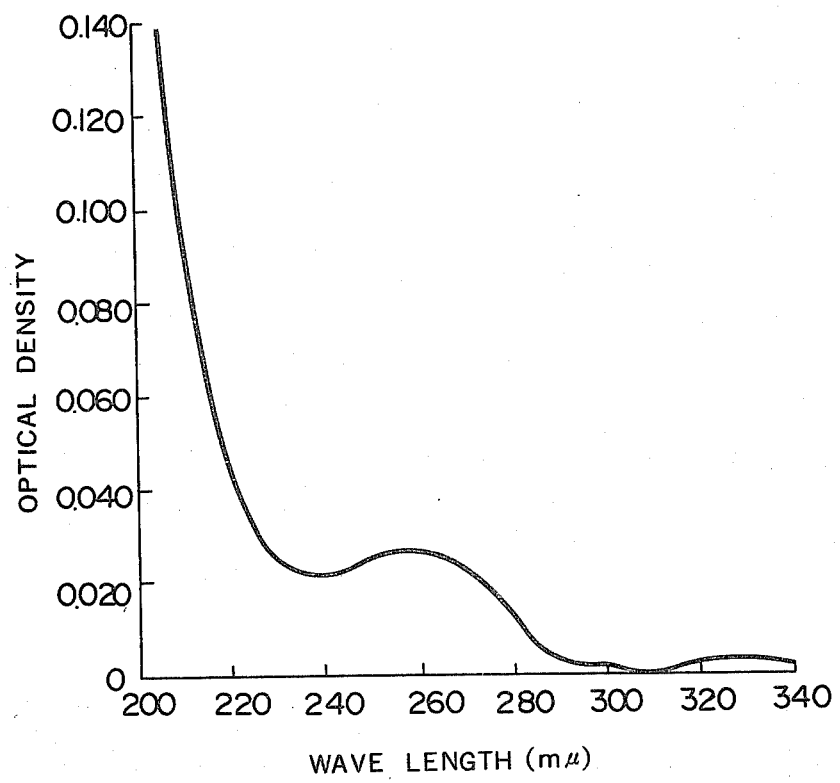

METHOD OF HUMAN CELL CULTURE

BACKGROUND OF THE INVENTION

1. Field of the Invention

The present invention relates to a method of culture of human cells which makes it possible to attain an efficient subculture of human somatic cells separated from an individual body for a long period of time.

2. Description of the Prior Art

It has heretofore been necessary to employ so-called subcultures of human cells for wide categories of biological studies of human beings including medicine, pharmacology and so on as an effective and practical means of conducting research. For this reason, in recent years subcultures of human cells has found application in various fields of research, such as in elucidation of the mechanism of cancer and in applications of the technique of cytofusion for the purpose of obtaining medically effective substances.

In general, for subculture of animal cells, it is necessary to use, with a few exceptions, a serum of, for example, an adult, neonate or fetus of cattle, horse, chicken, rabbit and other animal, in addition to the chemically defined synthetic culture medium consisting of amino acids, vitamins, minerals and so on. The reason for the indispensability of the serum is based on the fact that a matter that causes cell multiplicative growth (a substance other than the general nutritive materials) is contained therein, so that multiplication of cells is impossible without serum, owing to the lack of this causal matter.

It has been experienced, however, that a maximum of up to about 50-60 generation cycles is not exceeded in subcultures of normal human cells in vitro, even when cultivating such cells in a basal culture medium containing animal serum (ordinarily a cattle fetus serum). After passing this maximum number of successive generations, it has been observed either that alterations in the normal morphological aspect of the cells and in the hereditary genes were brought about, or that no further normal cell division was possible and the whole mass underwent biolysis, so that a succeeding generation cell strain has only been obtainable for a restricted number of successive generations. Therefore, renewed procurement of normal human cells has been inevitable.

BRIEF SUMMARY OF THE INVENTION

It is, therefore, an object of the present invention to provide a method of culture of human cells that resolves the difficulties described above.

It is another object of the present invention to provide a method of human cell culture in which all or a part of the animal serum, which has heretofore been incorporated in the culture medium as a necessary additive, can be dispensed with.

It is also an object of this invention to provide a method of culture of human cells which maintains successive cultivation in an efficient manner and maintains normal cell division over a long period of time, with a remarkable increase in the number of successive generations and without causing mutation of the cells.

These and other objects of the invention will appear more clearly from the following specification.

The method of cell culture according to the present invention is characterized by cultivation of human cells using a culture medium containing an extract of a micro algae.

DETAILED DESCRIPTION OF THE INVENTION

In this specification, the term "micro algae" means a unicellular algae or a near relative thereof, such as, for example, Chlorella, Scenedesmus, Spirulina or so on inclusive of natural living and cultivated ones types.

The extract of micro algae as indicated in this specification denotes an extract which results from an extraction of cells of one or more of said micro algae using an adequate solvent. As the solvent, an aqueous one is especially preferred. Among aqueous solvents, water itself and aqueous solutions containing dissolved therein acids, bases or organic solvents, may be exemplified.

In order to effect the extraction, the algae cells are brought into contact with the solvent, which may be heated or kept at ordinary temperature. A hot water extraction is recommended as a preferred and simple practice, in which the algae cells are suspended in water in an amount of 1-1,000 grams in dry weight of algae per liter of water and are kept at 50-150° C. for 0.5-120 minutes, preferably at 100° C. for more than 1 minute, and the suspension is then subjected to a procedure for separation of the cell bodies such as centrifugation etc., to leave an extract. The extract can be refined as needed by means of, for example, gel filtration, dialysis or like method.

The thus obtained extract of micro algae contains sugars, proteins, polysaccharides, nucleic acid and so on in the molecular weight range of from 1,000 to 1,000,000 and exhibits an activity for promoting multiplication in cultivated human cells.

The extract obtained as above can be used per se or in the form of a fraction formed by molecular weight fractionation thereof, which is a concentrate or a dry powder obtained by freeze-drying, spray-drying etc. Especially, a high molecular weight fraction formed by molecular weight fractionation containing sugars, proteins and polysaccharides and a dry powder thereof are preferred.

According to the present invention, cells of a human being are cultivated using a culture medium containing an extract of micro algae, wherein the culture procedures, the basal culture medium and so on may be identical with those used in conventional tissue culture. Thus, a known synthetic culture medium containing amino acids, vitamins and so on can be used as the basal culture medium, to which an extract of micro algae mentioned above is added in order to perform the cultivation of human cells under aspect conditions.

The human cells to be cultured include somatic cells taken out of an individual body of a human being, such as normal tissue cells and cancer cells.

The amount of the extract of micro algae added to the basal culture medium may be in the range from 0.1 to 400 μg and preferably in the range from 1 to 100 μg in dry weight of the extracted matter, per ml of the medium. The culture medium to which the micro algae extract has been added can be used per se for the cultivation. It is permissible to incorporate a serum as in a conventional culture medium. In this case, it is possible to reduce the amount of serum added, which has heretofore been assumed to amount to about 10% or more, to a value of up to 1 %.

When human cells are cultivated in a culture medium containing micro algae extract, not only is it possible to effect acceleration of cell multiplication, but it is also possible to maintain normal successive cultivation and to prolong the succession of generations without the appearance of any morphological or genetic mutations which have been inevitable in conventional culture methods, even those utilizing the addition of animal serum. Here, a comparable effect can be achieved even when the amount of addition of the animal serum, for which it has been admitted in general that it is necessary to employ 10% addition, is reduced down to one tenth of this amount, so that a great economization of the animal serum can be achieved.

Although the cause for rendering subcultures of human cells possible is not clear, it is to be assumed that the metabolism of the cells is stimulated and enhanced by the action of a biologically active substance which is intrinsic to the micro algae and is collected in the high molecular fraction of the micron algae extract containing especially glycoprotein, polysaccharide and similar materials.

As described above in detail, the present invention provides substantial advantages, namely, that the culture of human cells can be performed without employing or employing only a small amount of animal serum, which serum is unstable not only in composition but also in the supply thereof and is disadvantageous from the economic point of view, and that normal subculture of human cells can be carried out in an efficient and stable manner in a prolonged succession of generations without occurrence of mutations. It has been impossible to achieve such advantages by animal serum addition.

DESCRIPTION OF THE PREFERRED EMBODIMENT

The present invention is further explained by way of an example.

EXAMPLE 30 g of Chlorella powder were suspended in 1 l of water and were subjected to hot water extraction at 11° C. for 30 minutes. The suspension was then treated by centrifugation and the supernatant solution (corresponding to dry extracted matter of 4.5 g) was caused to undergo a molecular fractionation on a column of Sephadex G-25 (trade mark of Phamacia). The fractions with molecular weights above 3,000 were treated further by adsorption on a column of DEAE-cellulose (trade mark of Brown). The so adsorbed column was then eluted by a M/100 carbonate buffer. A fraction having a component with molecular weight over 70,000, a component with molecular weight in the range from 30,000 to 10,000 which was rich in neutral sugar and a component with molecular weight in the range from 10,000 to 3,000 which contained neutral sugar and protein in nearly equivalent proportions was obtained, which is denoted hereinafter as Fraction $A_1$. This Fraction $A_1$ was dried by freezing treatment to obtain 0.63 g of dry matter.

Then, $1 \times 10^2$ human fibroblasts were cultivated as the cell strain in a culture medium prepared by adding a cattle fetus serum (FCS) in an amount of 10% to the basal culture medium given in Table 1. This culture sector is denoted as Sector C. Further, in the same manner, $1 \times 10^2$ of this cell strain were cultivated in a culture medium prepared by adding said FCS in an amount of 1% and the above obtained Chlorella extract powder in an amount of 10 μg/ml-medium to said basal culture medium. This culture sector is denoted as Sector T.

Comparing the aspects of cell multiplication and of the succession of generations between the two culture sectors, it was observed that normal cell division was no longer maintained after a succession of 50-60 generation cycles (in about 10 months) resulting in biolysis of the cells in Sector C, whereas in Sector T, the subculture succession has been maintained to date over a succession of 90-120 generations, the cells remaining alive, without mutation of the cells in morphological and genetic respects, permitting about a two-fold extension of the succession of generations as compared with the conventional method.

TABLE 1

| Composition of the Basal Culture Medium | | | |
|---|---|---|---|
| Amino Acids | mg/l | Vitamins | mg/l |
| Ala | 400 | $B_1$ | 1.0 |
| Arg | 100 | $B_2$ | 1.0 |
| Asp | 25 | $B_6$ | 1.0 |
| Asn | 25 | $B_{12}$ | 0.005 |
| Cys HCl | 80 | Pantothenic acid | 1.0 |
| Glu | 150 | Nicotinamide | 1.0 |
| Gln | 300 | Biotin | 0.1 |
| Gly | 15 | Choline HCl | 5.0 |
| His | 30 | C | 1.0 |
| Ile | 150 | Folic acid | 1.0 |
| Leu | 400 | Inositol | 5.0 |
| Lys | 100 | | |
| Met | 80 | | |
| Phe | 80 | | |
| Pro | 12 | | |
| Ser | 80 | | |
| Thr | 100 | | |
| Trp | 40 | | |
| Tyr | 50 | | |
| Val | 85 | | |

What is claimed is:

1. A method for culturing human cells comprising culturing a sample of human cells in a nutritive culture medium for human cells, said culture medium containing an amount of an extract of microalgae sufficient to cause human cell multiplication, wherein said extract comprises substances having molecular weights in the range of 1,000 to 1,000,000, which substances include sugars, proteins, polysaccharides and nucleic acids.

2. A method according to claim 1, in which said microalgae is selected from the group consisting of Chlorella, Scenedesmus and Spirulina.

3. A method according to claim 2, wherein said extract is produced by extraction of said microalgae with water at a temperature from 50° C. to 150° C., for from 0.5 to 120 minutes.

4. A method according to claim 2, wherein said extract is produced by extraction of said microalgae with an aqueous solvent.

5. A method according to claim 4, wherein said aqueous solvent contains dissolved therein an additive selected from the group consisting of an acid, a base, and an organic solvent.

6. A method according to claim 4, in which said culture medium contains from 0.1 to 400 μg of said extract, calculated on a dry basis, per ml of said culture medium.

7. A method according to claim 6, wherein said extract is produced by extracting said microalgae with water at a temperature of from 50° C. to 150° C., for from 0.5 to 120 minutes, recovering the crude product that was extracted into said water, and then effecting molecular weight fractionation of said crude product to obtain said extract which is free of components derived from said microalgae having molecular weights of less than 3,000.

8. A method according to claim 6, wherein said human cells are selected from the group consisting of normal tissue cells and cancer cells of a human.

9. A method according to claim 6, wherein said microalgae is Chlorella.

10. A method as claimed in claim 6, wherein said culture medium further contains animal serum.

11. A method is claimed in claim 10, wherein said culture medium contains up to 1 percent by weight of animal serum.

12. A method for culturing human cells, which comprises: providing a nutrient culture medium containing, per ml of said culture medium, from 0.1 to 400 µg, calculated as the solids, of an aqueous extract of a microalgae selected from the group consisting of Chlorella, Scenedesmus, and Spirulina, said extract having been prepared by extracting said microalgae with water at a temperature of from 50° C. to 150° C., for from 0.5 to 120 minutes, so that said extract contains sugars, proteins, polysaccharides and nucleic acids having molecular weights in the range of from 1,000 to 1,000,000 and exhibits an activity for promoting multiplication of human cells; then placing said culturing on said culture medium a sample of human cells.

13. A method as claimed in claim 12, wherein said mixture is maintained at at least 100° C. for at least one minute, and the amount of said extract added to said culture medium is in the range of 1 to 100 µg of said extract, calculated as the solids, per ml of said medium.

14. A method according to claim 12, further including the step of fractionating said extract to remove therefrom components having molecular weights of less than 3,000 before adding said extract to said culture medium.

15. A method according to claim 12, wherein said human cells are fibroblasts.

16. A method of cell culture comprising:
suspending cells of one or more types of micro algae selected from the group consisting of Chlorella, Scenedesmus, and Spirulina in an aqueous solvent in an amount of from 1 to 1,000 grams in dry weight of said cells per liter of said aqueous solvent;
then maintaining the mixture of said cells and said solvent at a temperature in the range of 50° C. to 150° C. for 0.5 to 120 minutes;
then separating micro algae cell bodies from said mixture to form a micro algae extract from said mixture;
then adding said micro algae extract to a nutritive culture medium for human cells in an amount of 0.1 to 400 µg of said extract per ml of said medium; and
then cultivating human cells on said culture medium containing said micro algae extract to form a human cell culture.

17. A method according to claim 16, further including a step of fractionating said micro algae extract to remove components derived from said micro algae having molecular weights less than 3,000 therefrom before adding said extract to said culture medium.

* * * * *

UNITED STATES PATENT AND TRADEMARK OFFICE
CERTIFICATE OF CORRECTION

PATENT NO. : 4 468 460
DATED : August 28, 1984
INVENTOR(S) : Shoichiro Kumamoto

It is certified that error appears in the above-identified patent and that said Letters Patent is hereby corrected as shown below:

Column 5, line 30; change "said" (first occurrence) to ---and---.

Signed and Sealed this

Fifth Day of March 1985

[SEAL]

Attest:

DONALD J. QUIGG

*Attesting Officer*     *Acting Commissioner of Patents and Trademarks*